US006065301A

United States Patent [19]
Akazawa

[11] Patent Number: 6,065,301
[45] Date of Patent: May 23, 2000

[54] ACCESSORY STRUCTURE FOR VEHICLE AIR-CONDITIONER

[76] Inventor: Yasumasa Akazawa, 2-18-14, Higashishinmachi, Matsubara, Osaka, Japan

[21] Appl. No.: 09/346,131

[22] Filed: Jul. 2, 1999

[51] Int. Cl.[7] .......................................... F28G 9/00
[52] U.S. Cl. ................... 62/303; 62/78; 165/95
[58] Field of Search ......................... 62/303, 78; 454/337; 165/95

[56] References Cited

U.S. PATENT DOCUMENTS

| | | |
|---|---|---|
| 3,982,716 | 9/1976 | Trees . |
| 5,240,156 | 8/1993 | Sicotte . |
| 5,737,937 | 4/1998 | Akazawa ................................... 62/303 |

Primary Examiner—Henry Bennett
Assistant Examiner—Chen-Wen Jiang
Attorney, Agent, or Firm—Moonray Kojima

[57] ABSTRACT

The present invention relates to an accessory structure for vehicle air-conditioners for improvement of interior atmosphere by cleaning an evaporator or feeding aromatic or other functional solvents into vehicle air-conditioner adapted for taking in in- or out-side air through an air-conditioner air intake route, wherein a solvent injection means installed in the aforementioned route and a receiving member of a solvent source placed on the compartment side of the vehicle are communicated beforehand through a solvent feed route, so that the trouble and the work otherwise unavoidable for connecting the solvent source to the solvent feed route may be spared, permitting the solvent to be instantly fed to the solvent flow injection means.

8 Claims, 17 Drawing Sheets

ACCESSORY STRUCTURE FOR VEHICLE AIR-CONDITIONER

BACKGROUND OF THE INVENTION

1. Field of the Invention

The present invention relates to an accessory structure for vehicle air-conditioners intended for improvement in the atmosphere of the interior or compartment of an vehicle by cleaning their evaporator etc. or feeding aromatic or other functional solvents thereinto.

2. Description of the Prior Art

Heretofore, for improving the interior atmosphere by cleaning the evaporator or by supplying aromatic or other functional solvents, a configuration has been contemplated such that while a solvent injection nozzle is installed on the upstream side of a heat exchanger in the air-conditioning air intake route, and a hose connected to a nozzle led out into the compartment, a container filled with the solvent is installed near the driver's seat or front seat, and the hose is to be attached to the solvent discharge port of the filled container, when feeding the solvent therethrough. Since the filled container gains its solvent discharging force from the gas sealed in, overheating of the sealed-in gas resulting from irradiation of sunlight or temperature rise in the compartment has raised the problem of filled container disruption.

Moreover, as a means to solve the above-described problem, such disruption may be averted by locating the filled container on the bottom or side of the instrument panel (hereinafter abbreviated as inpane) where direct irradiation of sunlight may be averted, or in such other low temperature places inside the compartment for prevention of its disruption. However, in such locations, it is difficult to visually observe and check for sure from the driver's seat or front seat the end of the hose being led into the compartment, and therefore the position of the hose must be made sure by hand-touching, and then the hose and the container discharge port connected by a groping hand. This raised the problem of taking trouble and time in the work of connecting the hose to the discharge port of the filled container.

SUMMARY OF THE INVENTION

It is therefore the principal object of the present invention to provide an accessory structure for vehicle air-conditioners that enables instantly feeding the solvent to the solvent injection means, sparing the trouble and work of connecting the solvent source to the solvent feed route at the time of feeding the solvent, by preliminarily connecting the solvent flow injection means (nozzle) provided in the air-conditioning air intake route with the solvent source (filled container) installed in the compartment through the solvent feeding route (hose).

Another object of this invention is to provide an accessory structure for vehicle air-conditioner which enables the solvent source to be shielded from light and insulated from heat by means of a housing which surrounds whole or almost whole of said solvent source, thereby to restrain otherwise possible temperature rise of the solvent source.

A still another object of this invention is to provide an accessory structure for vehicle air-conditioners, wherein a cover member is provided at an opening of the housing for permission of opening/closing or pressing operation, so that whole of the solvent source is surrounded for improvement in its light shielding and heat insulation, while permitting the solvent to be fed without opening the cover member.

A further other object of this invention is to provide an accessory structure for vehicle air-conditioners, wherein the housing can be opened at one side, to permit the solvent source to be put in and out for facility in performing the work of putting in and out the solvent source or its replacement work.

A further other object of this invention is to provide an accessory structure for vehicle air-conditioners, wherein part (bottom) of the solvent source is exposed to the exterior of the housing, to permit the operation to be made without taking the solvent source out of the housing.

A further other object of this invention is to provide an accessory structure for vehicle air-conditioners, wherein there is provided on a receiving member located in the compartment a guide means for guiding the arrangement of the discharge port of the solvent source relative to said receiving member, thereby to ensure accurate connection of the discharge port of the solvent source to a joint of the receiving member.

A further other object of this invention is to provide an accessory structure for vehicle air-conditioner, wherein the guide means is provided for permission of its arrangement either in or out side of the discharge side periphery of the solvent source, thereby to permit the discharge port of the solvent source to be guided in the direction of having it to be communicated to the joint of the receiving member.

A further object of this invention is to provide an accessory structure for vehicle air-conditioner, wherein the guide means is provided with a tapered part to be abutted to the discharge side periphery of the solvent. source, to guide the solvent source into communication with the receiving member, thereby permitting the discharge port. of the solvent source to be guided to the optimal position for it to be joined the joint of the receiving member.

A further other object of this invention is to provide an accessory structure for vehicle air-conditioners,, wherein the guide means is displaceably provided so as to permit the operation of connecting the solvent source to the receiving member and the operation of discharging the solvent, thereby assuring simple and easy connection of the solvent source to the receiving member.

A further other object of this invention is to provide an accessory structure for vehicle air-conditioners, wherein the guide means is provided with a regulatory frame(s) for regulating into communication the receiving member and the solvent source in terms of their positions, thereby to ensure accurate mutual coupling.

Still other objects of this invention will become apparent from the embodiments later described.

DESCRIPTION OF THE PREFERRED EMBODIMENTS

Figure 1:
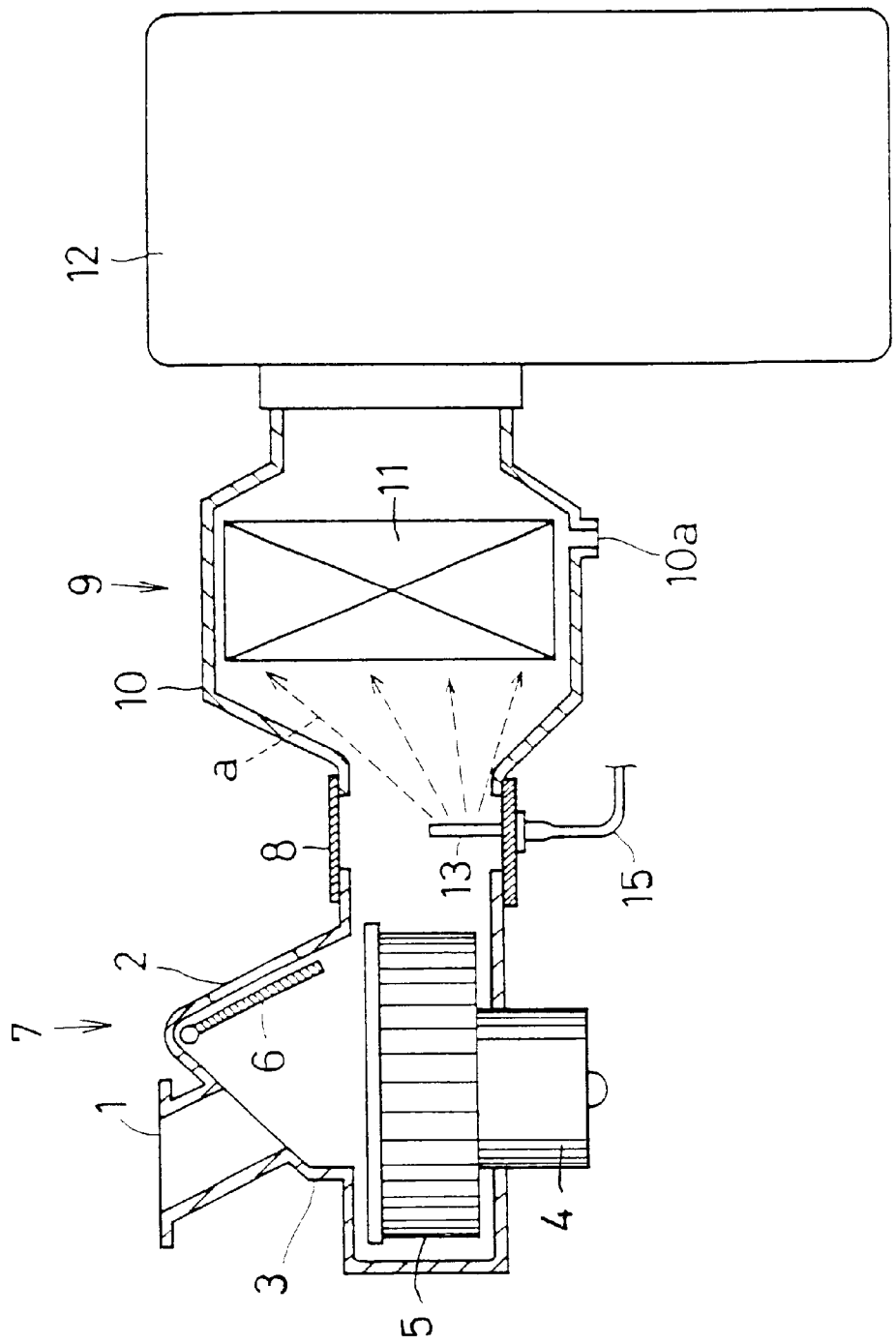
FIG. 1 is a side view showing an accessory structure for a vehicle air-conditioner of this invention.

Embodiments of this invention will now be described in detail hereunder with reference to the accompanying drawings:

These drawings depict accessory structures for a vehicle air-conditioner. First, describing the configuration of the vehicle air-conditioner in reference to FIG. 1, there is provided an internal/external air changeover box 3 having an external air intake port 1 and an internal air intake port 2. This box contains a fan 5 driven by a blower motor 4 and also a door 6 for selecting the air source to be taken into the air-conditioner.

Arranged next to the blower unit 7 composed as above-described is a cooler unit 9 linked thereto through a communication duct 8 (hereinafter called merely duct). The cooler unit 9 comprises an evaporator 11 (heat exchanger) inside its housing 10, and directly beneath the evaporator 11, there is formed a drain port 10a. The evaporator 11, being linked to the refrigeration cycle, acts to take heat off the ambience.

While a heater control unit 12 is communicatively joined next to the cooler unit 9, there is mounted on the duct 8 a nozzle 13 for injecting a solvent flow (a) toward nearly all over the front surface of the evaporator 11.

Figure 2:
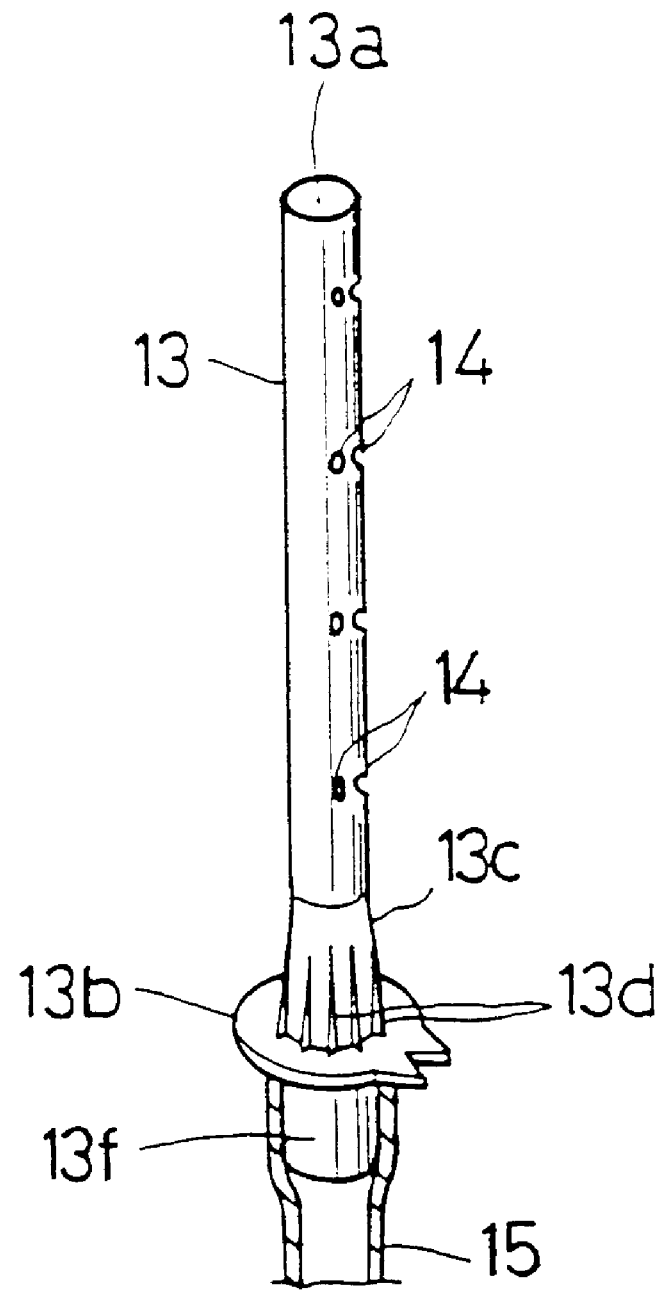
FIG. 2 is an explanatory diagram of the solvent injection means.

As shown in FIG. 2, the nozzle 13 has a shape of a relatively slender cylinder with its tip 13a closed, is made of a synthetic resin and formed with a series of paired injection ports 14, 14 which are oriented to produce jets in the dotted-line arrow directions, as shown in FIG. 1, in the location where it faces the front surface of the evaporator.

A nozzle neck 13c on its flange 13b side is formed in the shape of a tapered cylinder having gradually increasing diameters from its tip 13a side toward the flange 13b side, and it has formed on its outer circumferential surface a plurality of protrusions 13d triangular in cross-section which are to be engaged into and detained by the aperture formed in the duct 8 made of rubber. It is also to note that a means for joining the flange 13b to the duct may be jointly employed.

Further, the leading end of the rubber hose 15 (hereinafter merely hose in short) is securely fitted onto the joint 13f of the nozzle 13.

Figure 3:
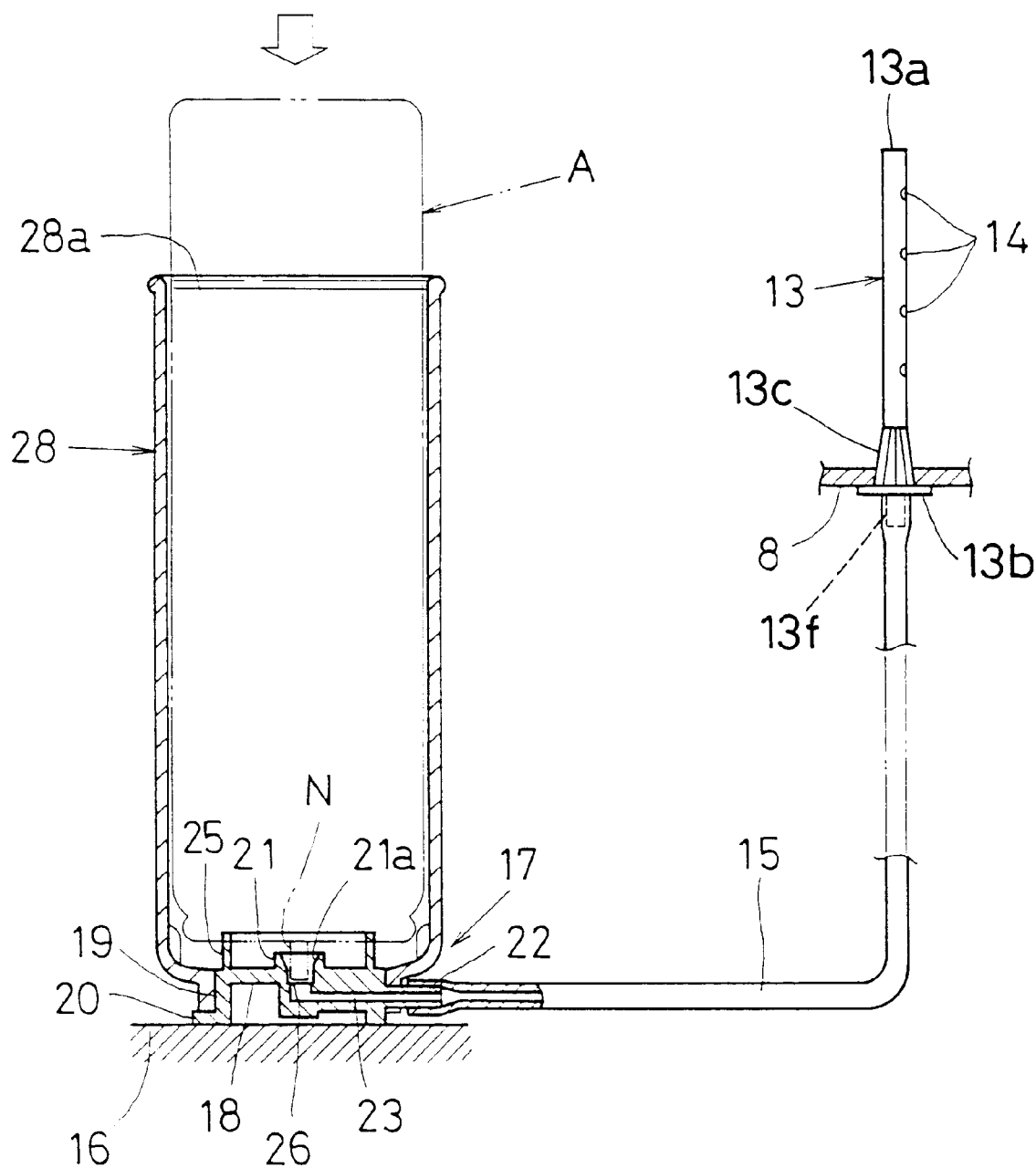
FIG. 3 is a side view of an embodiment showing its state with nearly whole of the container being accommodated in the housing.

The root end side of the above-described hose 15 is led out into the compartment, as shown in FIG. 3, is communicatively connected beforehand to a receiving member 17 made of a synthetic resin and which is securely installed (directed upward or downward, or horizontally or obliquely) by an appropriate means (bonding, bolting, clipping, pr double-coated taping) in a specified place in the compartment near the driver's seat or front seat, for example, bottom, side or front of an inpane 16, in- or out-side of a grove box or console box, shassis or interior material etc., where it will not be exposed to sun light and also where the temperature is relatively low.

The receiving member 17 is formed as a structure separated and independent from a solvent-filled container (hereinafter merely container in short) A as the solvent source, which comprises main plate 18, a flange 20 integrally formed therewith through a spacer 19, a nearly cylindrical joint 21 located at the center of the main. plate 18, a joint 22 outwardly projected from part of the outer periphery of the spacer 19, a passage 23 formed between these joints; on the other hand, a ring shape holder 25 for supporting the container A, and a nearly cylindrical housing 28 (or cover member) removably set in place or integrally formed on the outer periphery of the spacer 19.

The joint 21 is designed to connect and guide a nozzle N of the container A (a handy type container filled with gas) to the passage 23, when feeding the solvent, said joint 21 having formed a tapered hole 21a with its diameter gradually decreasing from outside to inside, and said tapered hole 21a having formed a ring shape stepped portion 26 for preventing overinsertion of the nozzle N at the innermost side thereof.

The joint 22 is formed to have a detent profile of a tapered cone multiple string structure, to securely hold the root end of the hose 15.

The housing 28, being formed of a thermally insulative material, accommodates nearly whole of the container A. The housing itself may be formed to be of a hollow construction, or the hollow space may be packed with any heat insulator or evacuated, or otherwise modified, thereby to enhance its heat insulation property to some extent.

One end side (lower side as shown in the drawing) of the housing 28 is removably set (screwed or otherwise fitted) on the outer circumference of the spacer 19, while the other end side (upper side as shown in the drawing) is opened wide enough to permit the container A to be put in or drawn out. The housing 28 may be formed integrally with the receiving member 17.

The solvent fluid (a) may be selected from liquid detergent, foamy cleaning liquid (a liquid containing water, phosphoric acid, Softanol 70, propylene glycol, and monomethyl ether MFG etc., mixed in appropriate proportions), cleaning water, aromatic, chemical, odor extinguisher, deodorant, sterile filter, bacteria-proof agent, sterilizer and mildew-proof agent, used singly or in combination (composite).

In the following, the action of the accessory structure of the vehicle air-conditioner composed as above-described will be set forth:

First, when cleaning the evaporator 11, as shown in FIG. 3, the container A is accommodated into the housing 28 mounted on the receiving member 17, the container A to be brought thereinto from its nozzle N side, while the nozzle N of the container A is to be communicated to the joint 21 of the receiving member 17 by guiding it by the inside wall surface of the housing 8.

After accommodating almost whole of the container in the housing 28, the bottom of the container projecting on the opening 28a side of the housing 28 is pressed, to push the container A onto the receiving member 17 fixed onto the inpane 16, and the solvent fluid (a) discharged from the nozzle N is fed into the passage 23 through the joint 21 of the receiving member 17. Then the solvent fluid (a) discharged from the nozzle N is fed to the nozzle 13 through the hose 15, to be jetted out from the injection ports 14 of the nozzle 13 toward nearly overall area of the front surface of the evaporator 11. Almost whole of complex shape fins etc. of the evaporator 11 may be cleaned well in this way, thereby enabling improvement in the interior atmosphere by the cleaning of the evaporator and the supply of aromatic or other functional solvents in correspondence with the type of solvent selected.

The fluid after used for the cleaning may be drained through the drain port located directly beneath the evaporator 11, or released from the vehicle, with a drain hose connected to the drain port 10a.

Arbitrary solvent fluids (a) may be fed to the nozzle 13 in appropriate amounts by exchanging the container A with other ones filled with any other solvent fluids (a) selected or in other ways. With regard to the sequence of using the solvent fluids, the foamy detergent, chemicals like sterile filtration or bacteria proof agents etc. or the foamy detergent, cleaning water and chemicals may be used in the order mentioned; or other detergents which are not foamy and bacteria proof agents may be used in the order mentioned. Furthermore, the evaporator may be dried by feeding air, warm air, hot air or cold air etc. from the root end opening of the hose 15 after the cleaning operation.

Particularly, if the solvent fluid (a) jetted from the nozzle 13 is set to a foamy fluid, the foamy fluid will be blown to the whole range of the front surface (that is to say the whole area) of the evaporator 11 on the upstream side, permitting almost whole of the evaporator 11 to be efficiently cleaned to the innermost part thereof by the foamy fluid by dint of the circulation of the air-conditioning air.

Since in this way the container A accommodated in the housing 28 is connected beforehand to the nozzle 13 through the hose 15, the trouble or work for connecting the container A to the hose 15 is spared, when feeding the solvent fluid (a) to the nozzle 13. Then the container is to be stationary set at a location where easy access from the driver's seat or front seat is permitted for simple and facile operation of the container A, so that instant feed of the solvent fluid (a)to the nozzle 13 through the hose may be assured in time of need.

Further, since almost whole of the container A is surrounded by the housing 18, its light shielding and heat insertion may be ensured, and consequently its temperature rise inhibited, making for its protection from disruption and damage. Also even when the temperature in the compartment has fell down, it will be shielded from the cold air, so that the solvent fluid (a) inside the container A may be guarded against coagulation.

Furthermore, since the operation of feeding the solvent fluid (a) is performed by pressing the bottom of the container A projecting on the opening 28a side of the housing 28, the operation may be performed without drawing out the container A from the housing 28.

Figure 4:
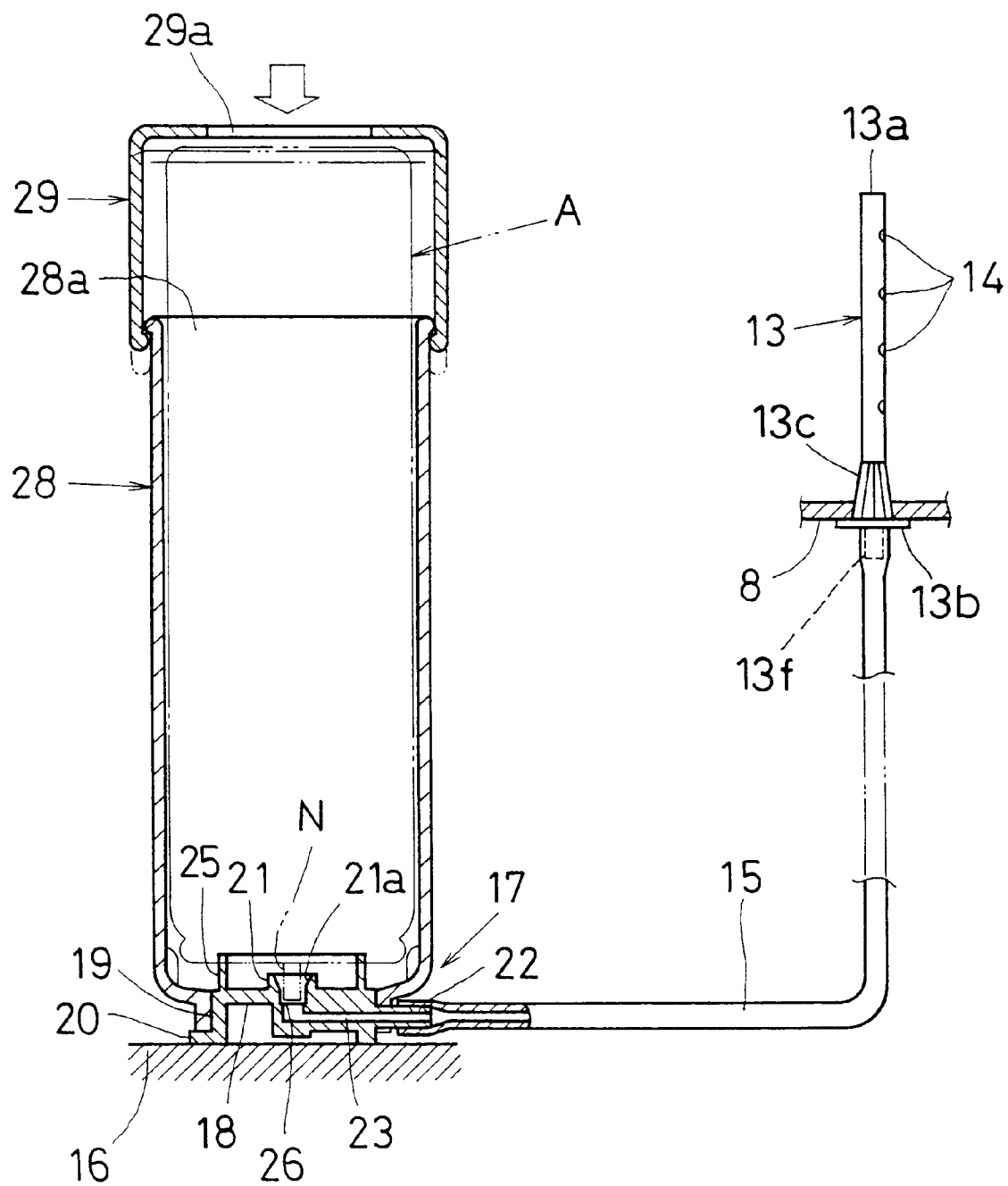
FIG. 4 is a side view of an embodiment showing whole of the container being accommodated in the housing.

FIG. 4 shows another embodiment in which a cover member 29 is removably and slidably fitted with some idling margin onto the outer surface of the opening 28a of the housing 28, thereby to surround the whole of the container A with the housing 28 and the cover member 29, so that its light shielding and thermal insulation are improved from those of the previous embodiments, further ensuring prevention of possible disruption and damage of the container.

Moreover, since the cover member 29 is pressed onto the bottom of the container A, or the exposed surface of the bottom of the container A is pressed through an opening 29a formed in the cover member 29, the solvent fluid (a) feeding operation is facilitated, with the trouble of opening/closing the cover member 29 spared. It is also to note that the cover member 29 may be open/close-ably joined to the housing 28 through such a connection means as a flexible piece, hinge etc.

Figure 5:
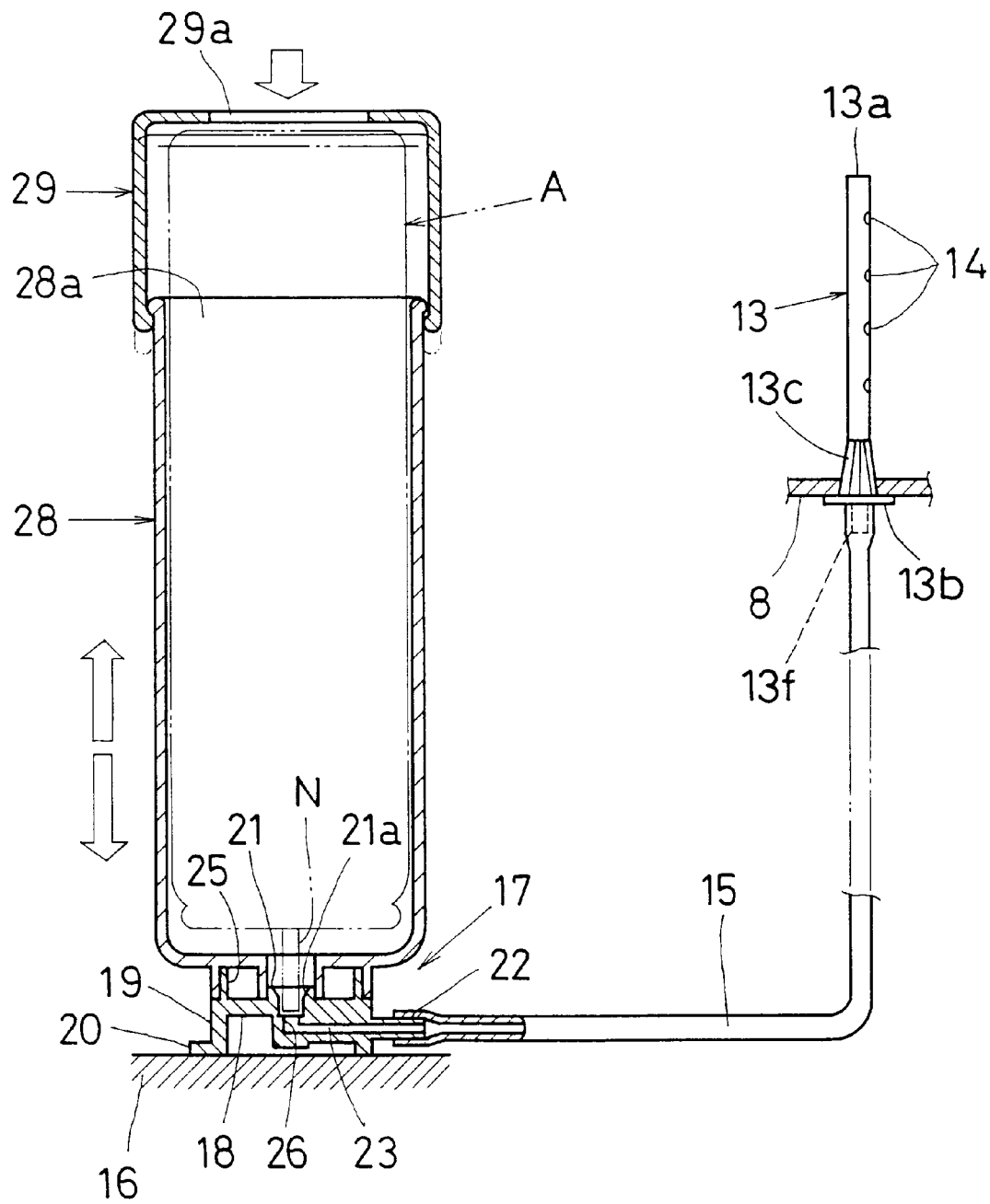
FIG. 5 is a side view of an embodiment showing the housing being removably installed.

FIG. 5 shows still another embodiment, in which the housing 28 is removably mounted on the receiving member 17 in communication therewith, and the container A is accommodated in an enclosure composed of the housing 28 and the cover member 29 which surround it. With whole of the container A surrounded by the housing 28 and the cover member 29, its light shielding and heat insulation are improved, providing nearly similar action and effect as the embodiment of FIG. 4.

Moreover, since with one end side (the bottom side, as shown) of the housing 28 fixed to the holder 25, the nozzle N of the container A which has been projected from the center of the one end side of the housing 28 is inserted and fixed in the joint 21 in communication therewith, making for simple and facile connection of the nozzle N.

Figure 6:
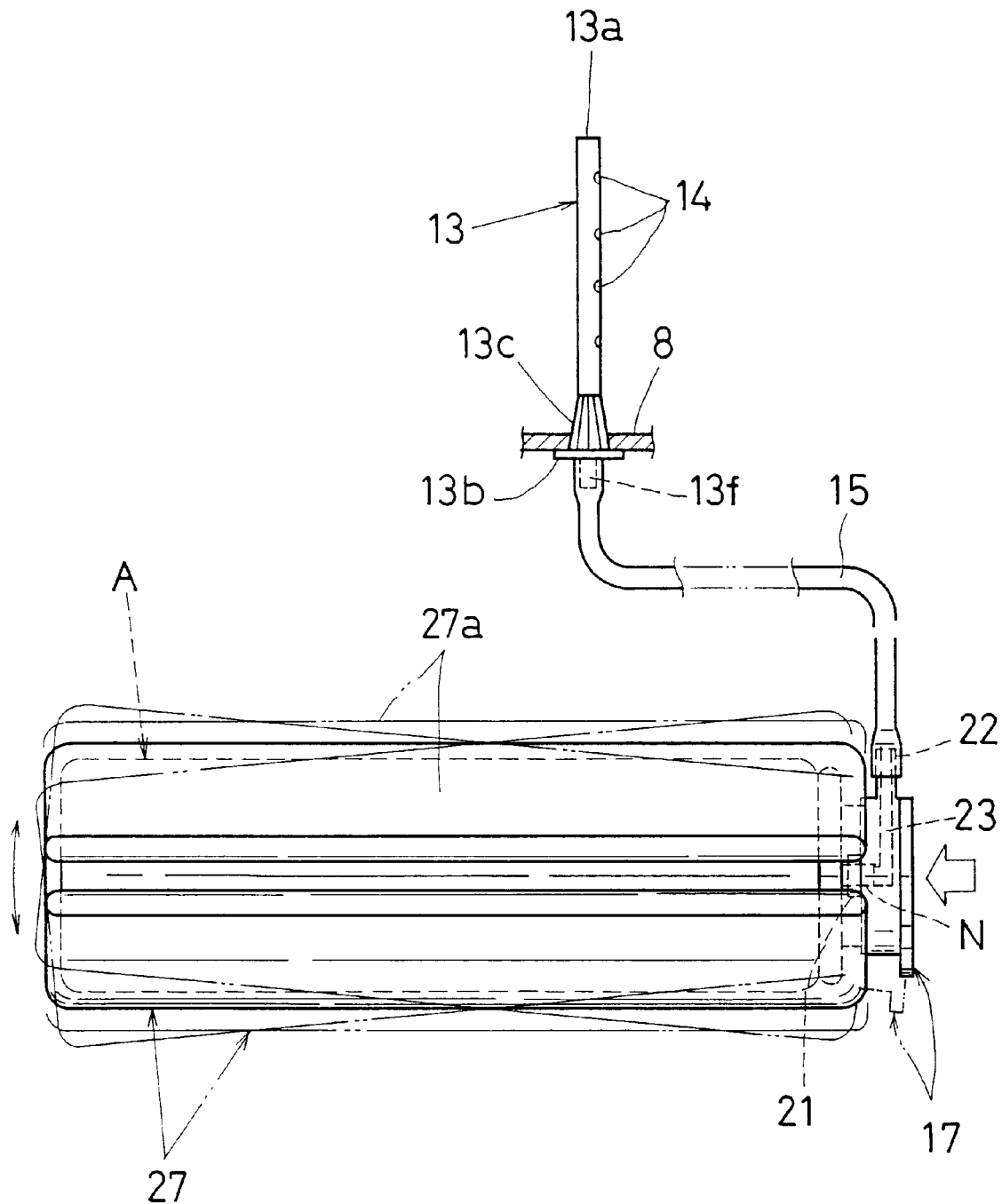
FIG. 6 is a side view of an embodiment showing nearly whole of the container being held by the housing.
Figure 7:
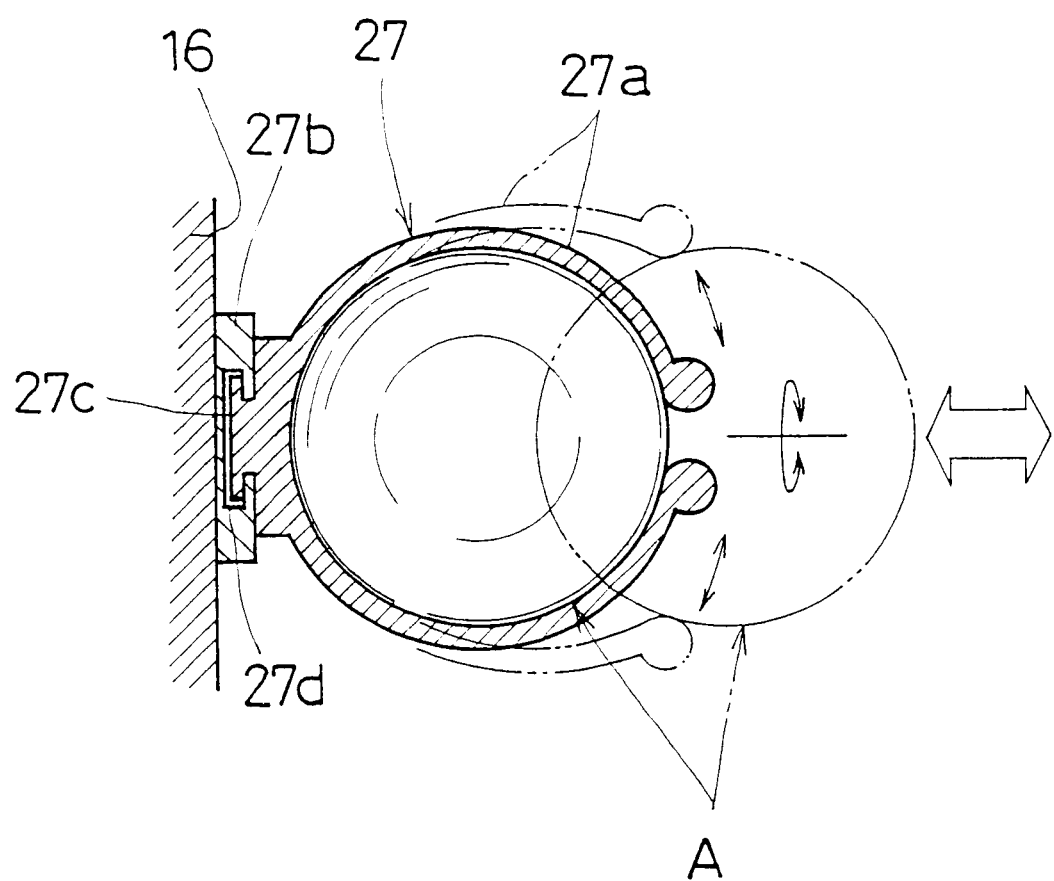
FIG. 7 is a sectional view showing the state of the housing holding the container.

FIGS. 6 and 7 show a further other embodiment, in which the container A is brought into a nearly cylindrical housing 27 from the side or the rear thereof The housing 27 is formed of a thermally insulative material or of a thermally insulatable construction. It is formed with a size large enough to surround and hold nearly whole of the container A.

The sides of the support 27a configuring the housing 27 are constructed to be open/close-able to its open state which permits the container to be taken in or out and to its closed state for holding the container A. On the other hand, the base 27b is fixed to the inpane 16 by such a locking means as a clip etc. A pivot 27c formed at the back of the support 27a is engaged into a slot 27d provided in the base 27b, thereby to permit the support 27a to be turnable in any directions or to any angles, with the pivot 27c as the center.

Since the above-described container (a) is taken into or out of the support 27a of the housing 27 from its side, the work of taking in or out the container A can be performed simply and easily, even when it is difficult to bring into or take out the container from the longitudinal end of the housing 27. Further, with nearly the whole of the container A surrounded by the housing 27, light shielding and heat insulation of the container is ensured., to protect it from disruption and damage, thereby achieving nearly the same action and effect as in the previous embodiments.

Further, since after turning the container to any arbitrary direction or angle, the receiving member 17 which has been securely held beforehand on the nozzle N side is pressed, to feed the solvent fluid (a) discharged from the nozzle N to the nozzle 13 mounted on the duct 8, the pressing operation of the receiving member 17 (or nozzle N) may be performed from any arbitrary direction, simplifying and facilitating the feeding operation of the solvent fluid (a). In this way, the container may be turned to any direction or angle suitable for the operation.

In this regard, it is also permissible to make the bottom side of the container A pressable, with the receiving member 17 fixed to the inpane 16, or to use a configuration such that a detent (not shown in the drawings) provided contiguous to the support 27a is to be engaged with the bottom side of the container A, for detaining the movement of the container A. It is to note that while detailed description is omitted, with same reference codes used for the identical parts of the previous embodiments in FIGS. 4–7, in the embodiment of FIGS. 6 and 7, the root end of the hose 15 may be directly coupled to the nozzle N, with the receiving member 17 omitted, and the nozzle may have any configurations such as of expanded head type having nozzle holes or of gun injection type nozzle, besides the stem type shown.

Hereinabove described are embodiments corresponding to claims 1–5. In the following embodiments corresponding to claims 6–10 are described in reference to FIGS. 8–17. Detailed description is omitted in regard to FIGS. 8–17, with the same reference codes attached to the identical parts to those in the previous FIGS.

Figure 8:
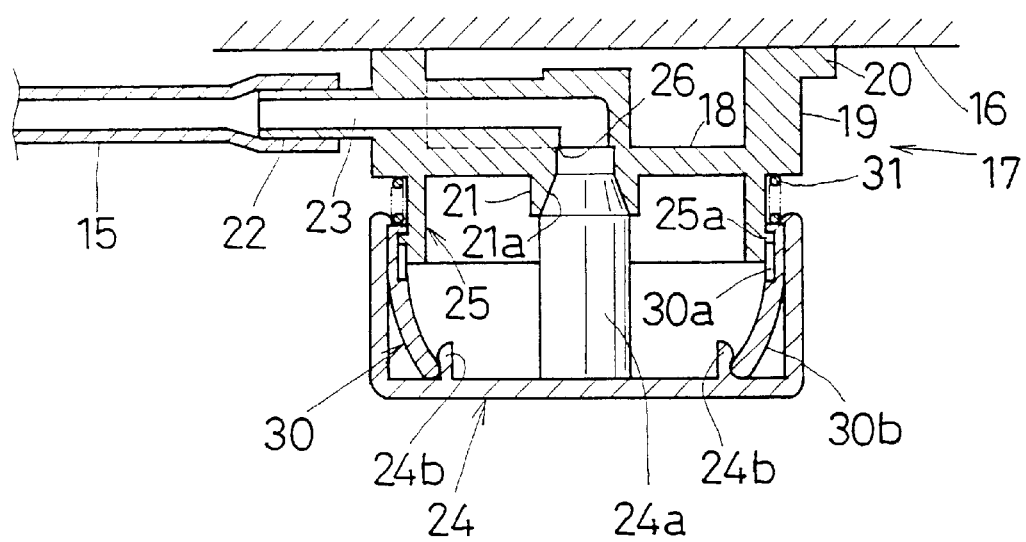
FIG. 8 is a sectional view showing the construction of the receiving member.
Figure 9:
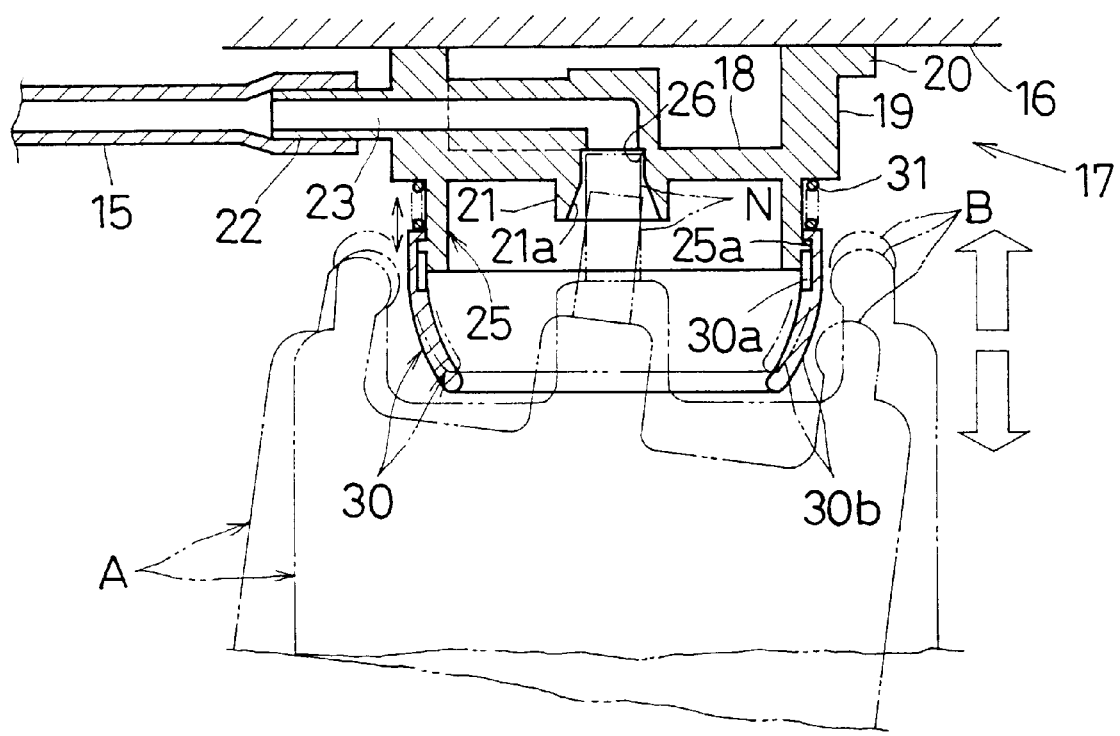
FIG. 9 is a sectional view showing the coupling state of the container.

Referring to FIG. 8, there is provided a cover 24 for covering the opening side of the receiving member 17. This cover member 24 is removably fitted or screwed on the outer surface of a guide member 30 (inner guide), has a protrusion 24a for closing the passage 23 of the joint 21, or particularly the tapered hole 21a, formed at the inside center for prevention of dust or other inclusions coming in to stick on or pass through the passage 23 of the joint 21. Sideways apart from the protrusion 24a, there is formed a hook 24b to engage the opening side peripheral edge of the guide member 30, and the outer circumferential surface of the cover member 24 is roughened (for example knurled) for ease of attachment/detachment of said member 24.

It is to note that the cover member 24 may be open/close-ably coupled to the receiving member 17 through such a coupling means as a flexible piece, hinge, etc.

The guide member 30, designed to guide the nozzle N of the container A in inserting it into the passage 23, is slidably mounted on the outer circumferential surface of the holder 25.

A bump 25a protruded from the outside surface of the holder 25 is fit in a groove 30a formed in the inside surface of the guide member 30, thereby to hold the guide member 30 on the holder 25 in detention. A coil spring 31 attached on the outer circumferential surface of the holder 25 is urged in the direction of returning the guide member 30 to the position indicated by a real line in FIG. 8.

The external surface of the guide member 30 is formed with dimensions that allow it to be inserted in the inside of the peripheral edge B (sealing part) of the container A side, the guide member having a guide 30b forming a smooth curve from its leading end side toward its root side wth gradually increasing diameters.

In this embodiment, the receiving member 17 is separated and independent from the container A, so that the container A may be accommodated in a grove box or console box, etc. of the vehicle.

In this regard, the above mentioned elements 13, 15 and 17 may be handled as a kit, so that each of the aforementioned elements 13, 15 or 17 may be installed on the vehicle after commissioned, or they may be integrally mounted on the vehicle beforehand when manufacturing the vehicle.

In the following, the action of the accessory structure for vehicle air-conditioner comprized as hereinabove described will be described:

When cleaning the evaporator 11, after removing the cover member 24 from the guide member 30 shown in FIG. 8, the guide member 30 is relatively inserted in the inside of the peripheral edge B of the container A, and then the nozzle N of the container A is insertingly guided into the joint 21 by the aid of the guide 30b of the guide member 30, whereby not only the nozzle N is communicatively linked to the passage, guided by the tapered hole 21a of the joint 21, but the guide member 30 is slid in defiance of a coil spring 31, to permit the receiving member 17 and the container A to be coupled.

Figure 10:
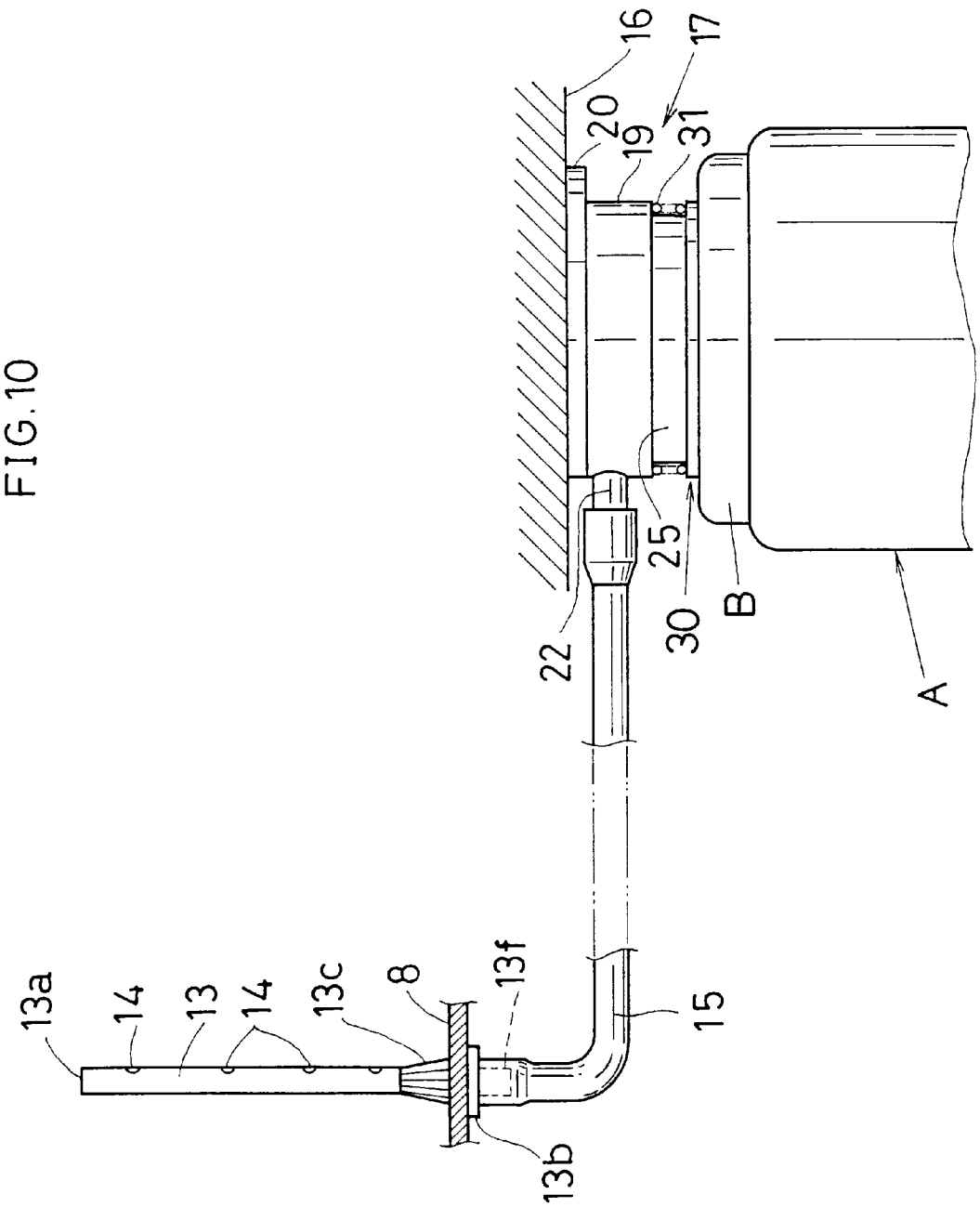
FIG. 10 is a side view showing the connection state between the nozzle, receiving member and the container, respectively.

Next, as shown in FIG. 10, the container A is moved in the direction of pressing it onto the receiving member 17, thereby getting it slide on the guide member 30, and discharging the solvent fluid (a) through the nozzle N. Then the solvent fluid (a) is fed to the hose 15 through the passage 23, to be ejected from the injection ports 14 of the nozzle 13 toward nearly whole range of the front surface of the evaporator 11. Accordingly, almost whole of complex figured fins etc. may be well cleaned, enabling amelioration of vehicle interior atmosphere by cleaning the evaporator 11 or feeding aromatic or other functional solvents in correspondence with the types of solvents.

As described hereinabove, when loading the container A on the receiving member 17 securely installed inside the compartment, the guide member 30 of the receiving member 17 is inserted in the peripheral edge B of the container A, to be arranged there, thereby guiding the nozzle N into the state of communicating with the joint 21 of the receiving member 17. Therefore, even if the receiving member 17 is located in a part of the interior where it is hardly visible, the work of coupling the nozzle N with the joint 21 of the receiving member 17 may be simplified and facilitated, for the benefit of infallible solvent feed.

Figure 11:
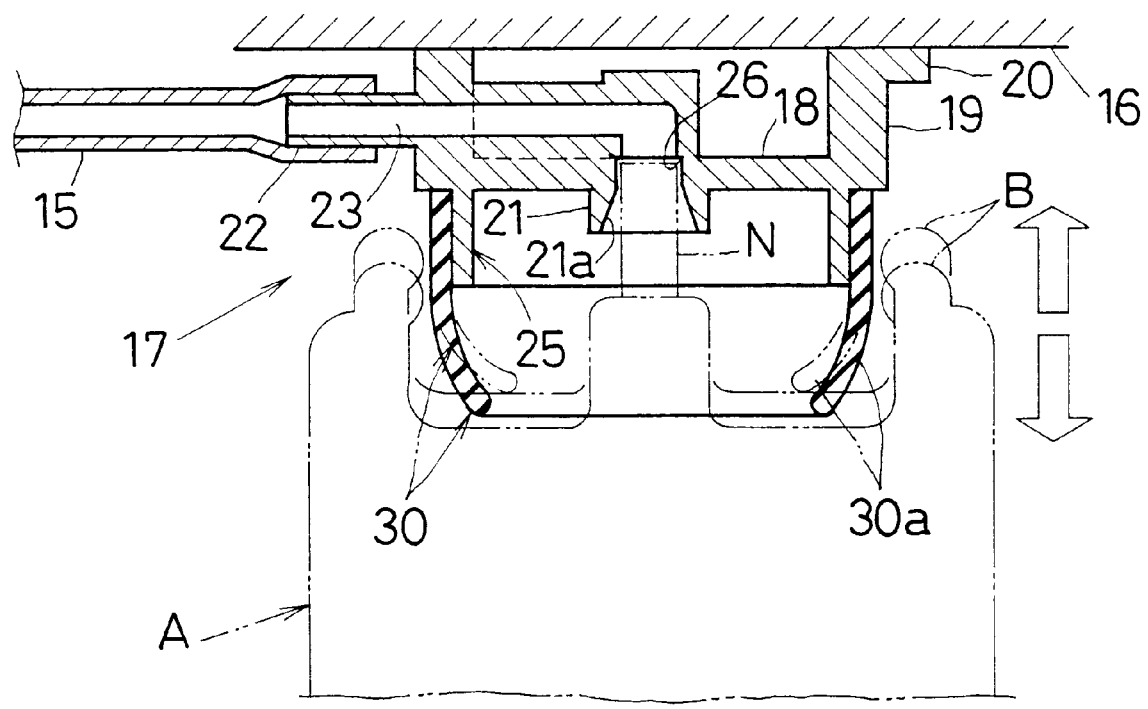
FIG. 11 is a sectional view of an embodiment showing a deformable guide member being fixed.

FIG. 11 shows another embodiment, wherein the guide member 30 is integrally fixed to or formed with the holder 25 of the receiving member 17, and the guide member 30 is formed of an elastic body like synthetic rubber, soft resin etc. or a flexible member like resin or metal piece etc.

When loading the container, the guide member 30, which is relatively inserted inside the peripheral edge B of the container A, is elastically or flexibly deformed, and the nozzle N of the container A is guided by the guide member 30 into the state of communicating with the passage 23. Accordingly, similarly as described hereinabove, the work of coupling the nozzle N of the container A with the joint 21 of the receiving member 17 is simplified and facilitated, thus achieving nearly similar action and effect to those of the preceding embodiments.

Figure 12:
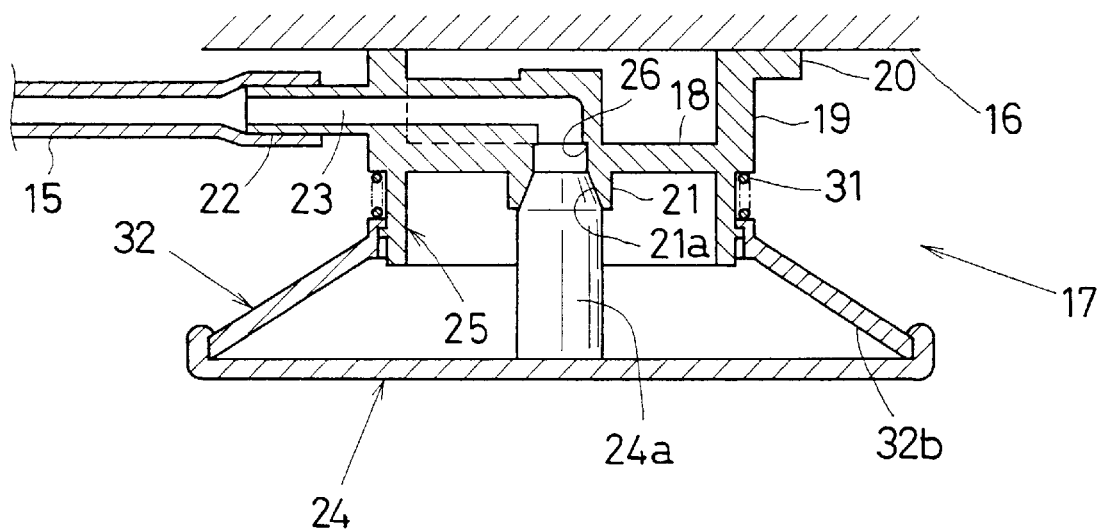
FIG. 12 is a sectional view of an embodiment showing a trumpet shape guide member being attached.
Figure 13:
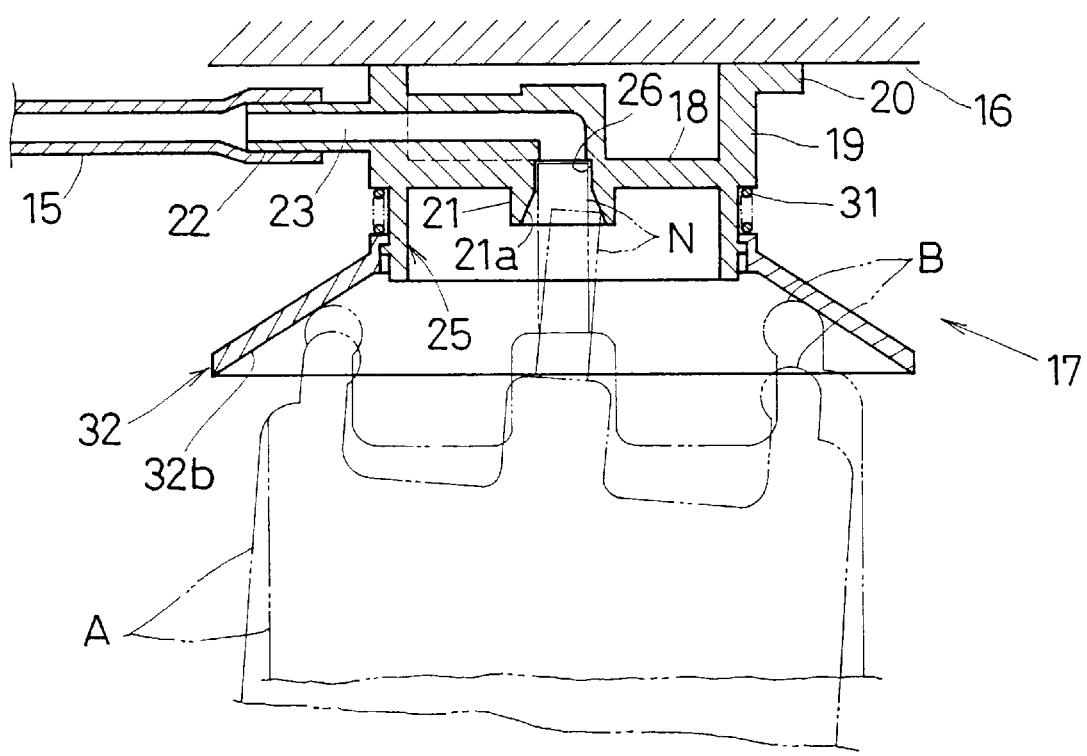
FIG. 13 is a sectional view showing the connecting state of the container.

FIGS. 12 and 13 show still another embodiment, wherein a trumpet or tapered cone shape guide member 32(outerguide) is slidably mounted on the holder 25 of the receiving member 17, the inner surface of the guide member 32 facing the peripheral edge B of the container A is formed as a tapered portion 32b sloped toward the center of the joint 21, and a cover member 24 is open/close-ably fitted on the outer edge of the opening side of the guide member 32.

When loading the container, if as shown in FIG. 13, the nozzle N of the container A supposedly inserted into the joint 21 of the receiving member 17 from oblique direction, the peripheral edge B of the container is abutted onto the tapered portion 32b of the guide member 32, thereby guiding the nozzle N by turning its direction into communication with the joint 21 of the receiving member 17. Then the nozzle N is brought to the optimal position for feeding the solvent to the joint 21, thus always ensuring infallible coupling operation. In this way nearly similar action and effect are achieved as in the preceding embodiments.

Figure 14:
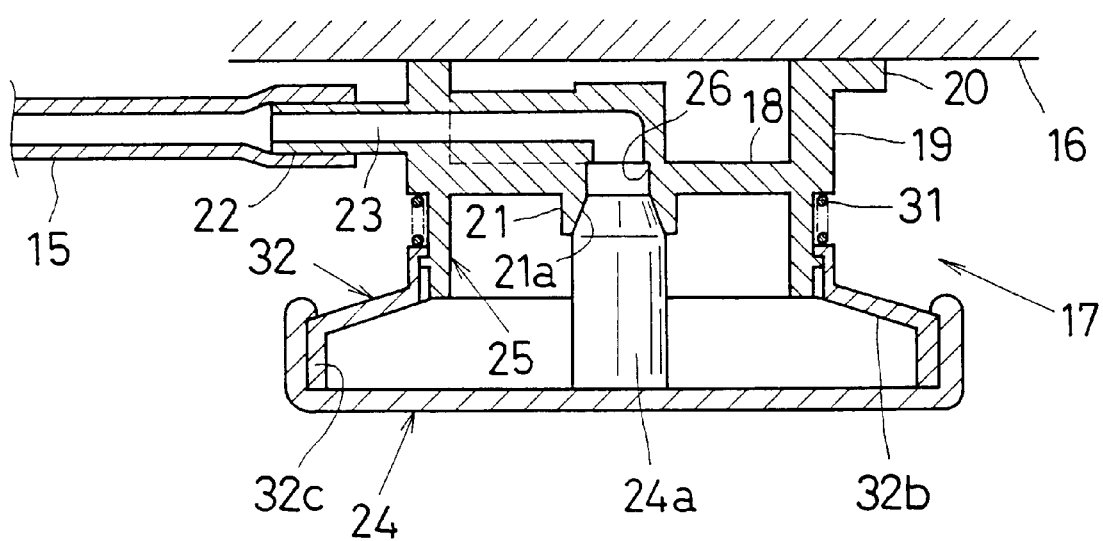
FIG. 14 is a sectional view of an embodiment showing a regulatory frame formed on the outer periphery of the guide member.
Figure 15:
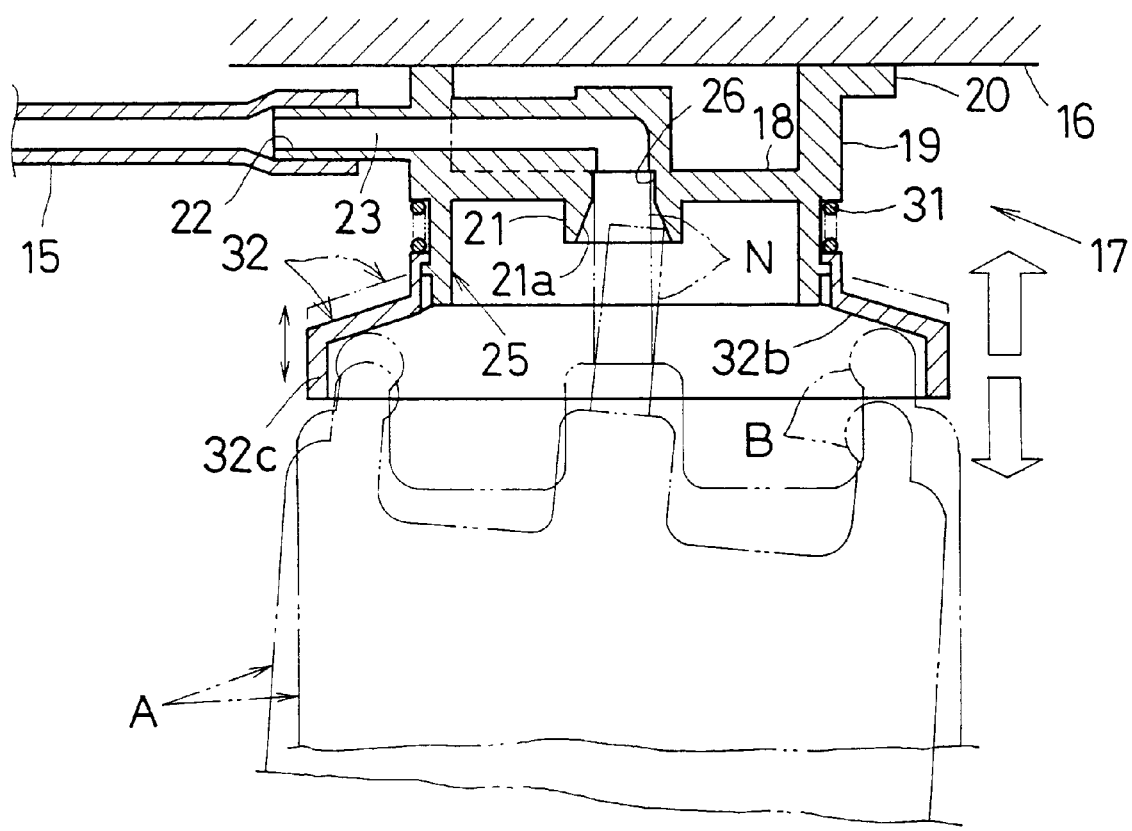
FIG. 15 is a sectional view showing the connecting state of the container.

FIGS. 14 and 15 show still another embodiment, wherein on the outer circumference of the guide member 32, there is formed a regulatory frame 32c, the regulatory frame 32c being formed contiguously from the guide member 32 or partially in the circumferential direction thereof, and a cover member 24 is open/close-ably mounted on the outer surface of the regulatory frame 32c of the guide member 32.

When loading the container, as shown FIG. 15, the peripheral edge B of the container A is abutted onto the inside surface of the regulatory frame 32c and the tapered portion 32b, thereby guiding the nozzle N of the container A to be inserted into the joint 21 of the receiving member 17, while regulating the position of the container A by means of the regulatory frame 32c. In this way, nearly the similar action and effect to those of the preceding embodiments are achieved.

Figure 16:
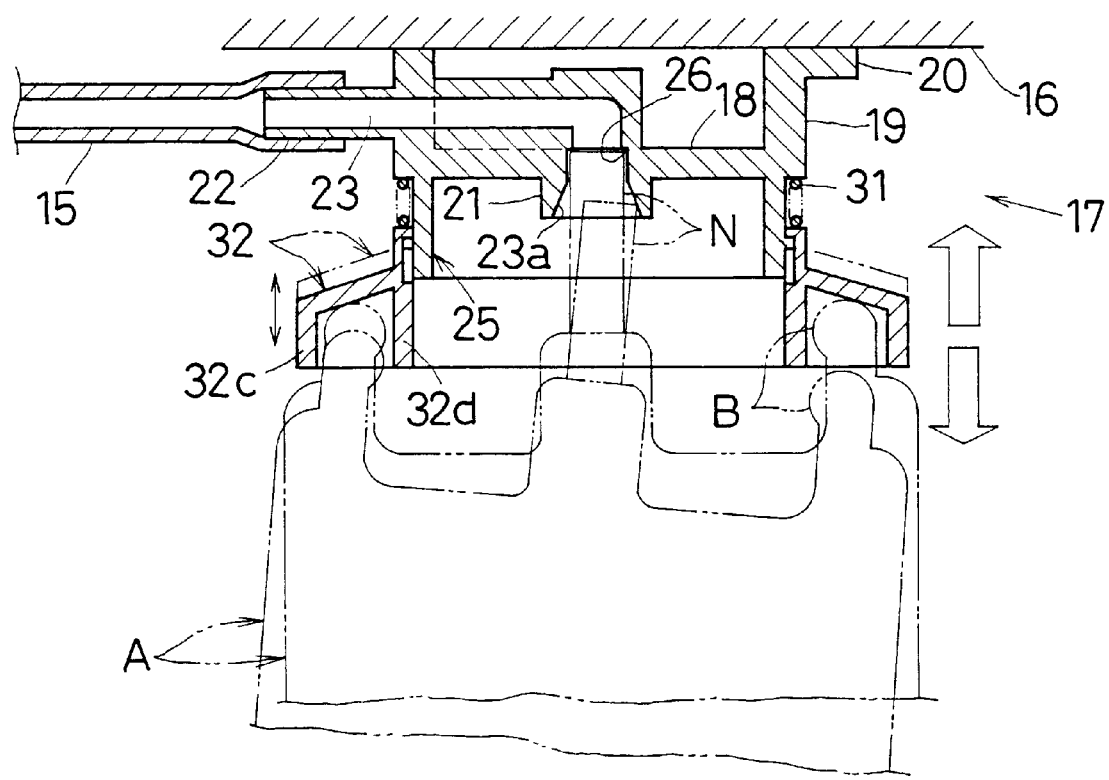
FIG. 16 is a sectional view of an embodiment showing regulatory frames on inner and outer peripheries.

FIG. 16 shows still another embodiment, wherein along the inner circumference of the guide member 32, there are provided an outer regulatory frame 32c and an inner regulatory frame 32d in parallel thereto. When loading the container, as shown in this figure, the peripheral edge B of the container A is inserted between the inner and outer regulatory frames 32d and 32c, thereby holding the peripheral edge B by respective regulatory frames 32c and 32d. Then play of the container A is forestalled, and the nozzle N of the container A may be accurately and positively inserted into the joint 21 of the receiving member 17, there to be seated in place. In this way, nearly the similar action and effect to those of the preceding embodiments are achieved.

Figure 17:
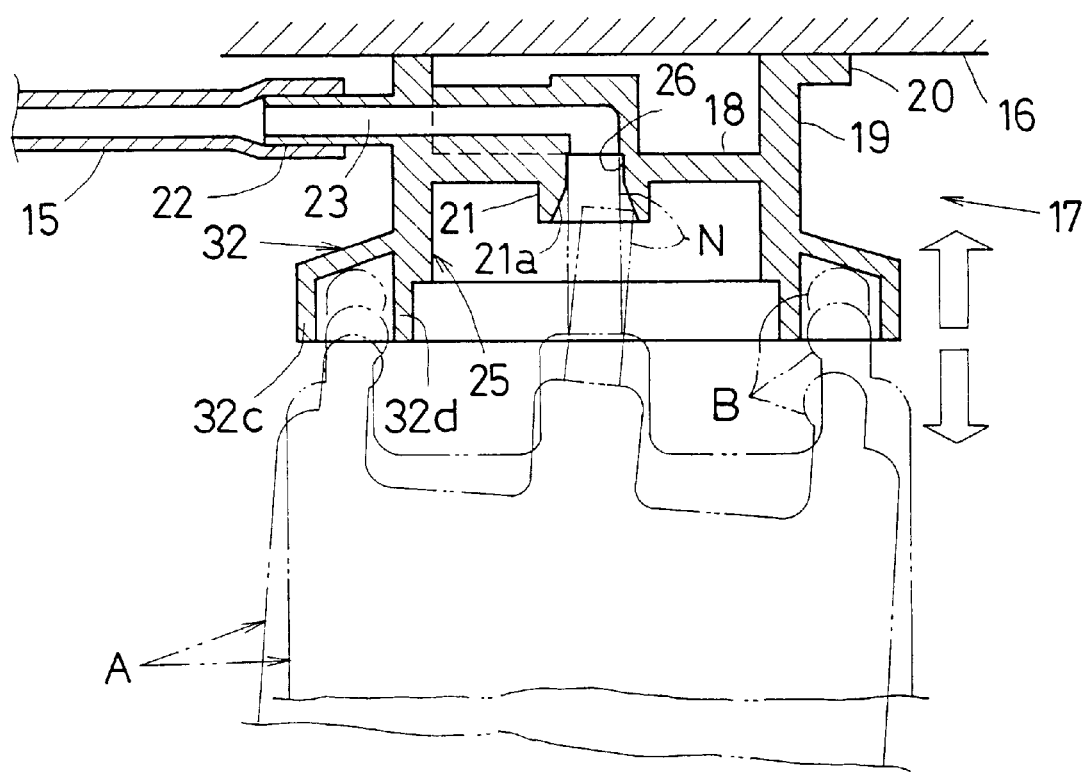
FIG. 17 is a sectional view of an embodiment showing the guide member formed as part of the holder.

FIG. 17 shows still another embodiment, wherein the guide member 32 with respective regulatory frames 32c and 32d is integrally formed with or fixed to the holder 25 of the receiving member 17; the peripheral edge B of the container A is inserted between regulatory frames 32c and 32d formed as parts of the guide member 32, to hold it in operable state. In this way, nearly similar action and effect to those of the preceding embodiments are achieved. It is to note that the outer regulatory frame 32c only may be formed integral with the holder 25.

Discussing the constitution of this invention in correspondence with the above described embodiments, the air-conditioning air intake route of this invention corresponds to the route from the air intakes 1 and 2 to the evaporator 11 of the embodiments, then similarly, the solvent flow injection means to the nozzle 13, the solvent feeding route to the hose 15, the solvent source to the container A, the housing to the housings 27 and 28, the discharge port of the solvent source to the nozzle N of the container A, and the guide means to the guide members 30 and 32, The scope of this invention is not limited to the configurations of the above-described embodiments.

For example, as solvent feed routes replacing the hose 15, use may be made of any resin or metal pipe, and the construction of the nozzle 13 is not limited to the one shown in the embodiments.

What is claimed is:

1. In a vehicle air-conditioner cleaning apparatus comprising:
   a solvent spraying means disposed within an air intake route of said vehicle air-conditioner;
   holder means disposed within said vehicle for holding a solvent container; and
   connecting means for connecting said holder means to said spraying means; the improvement comprising:
   housing means attached to said holder means; and
   removable reservoir means inserted and held within said housing means for supplying said solvent through said connecting means to said spraying means, said reservoir means being said solvent container.

2. The apparatus of claim 1, wherein said housing means comprises a base part attached to said holder means, and a covering fit to said base part.

3. The apparatus of claim 1, wherein said housing means comprises an elongated structure disposed vertically, and wherein said reservoir means comprises an elongated vessel disposed vertically within said vertically disposed structure of said housing means so that said solvent flows downward into said connecting means.

4. The apparatus of claim 1, wherein said housing means comprises an elongated structure disposed horizontally, and wherein said reservoir means comprises an elongated vessel disposed horizontally within said horizontally disposed structure of said housing means so that said solvent is caused to flow horizontally into said connecting means.

5. In a vehicle air conditioner cleaning apparatus comprising:
   a solvent spraying means disposed within an air intake route of said vehicle air conditioner;
   holder means disposed within said vehicle for holding a solvent container; and
   connecting means for connecting said holder means to said spraying means; the improvement comprising:
   said holder means comprising:
      receiving means to which said solvent container is removably connected and held to receive solvent for supply through said connecting means to said spraying means; and
      guide means for guiding an opening of said solvent container to said receiving means, said guide means being disposed to be inside or outside a peripheral edge of an opening to said solvent container.

6. The apparatus of claim 5, wherein said guide means comprises a tapered part which abuts and removably holds said opening of said solvent container within said receiving means of said holder means.

7. The apparatus of claim 5, wherein said guide means comprises a resilient part for resiliently and removably holding said opening of said solvent container within said receiving means of said holder means.

8. The apparatus of claim 5, wherein said guide means comprises a frame for positioning and removably holding said opening of said solvent container within said receiving means of said holder means.

* * * * *